United States Patent
Kunos et al.

(10) Patent No.: US 7,109,245 B2
(45) Date of Patent: Sep. 19, 2006

(54) VASOCONSTRICTOR CANNABINOID ANALOGS

(75) Inventors: George Kunos, Bethesda, MD (US); Raj K. Razdan, Gloucester, MA (US)

(73) Assignees: The United States of America as represented by the Secretary of the Department of Health and Human Services, Washington, DC (US); Organix Inc., Woburn, MA (US)

( * ) Notice: Subject to any disclaimer, the term of this patent is extended or adjusted under 35 U.S.C. 154(b) by 0 days.

(21) Appl. No.: 10/486,810

(22) PCT Filed: Aug. 14, 2002

(86) PCT No.: PCT/US02/26050

§ 371 (c)(1), (2), (4) Date: Feb. 13, 2004

(87) PCT Pub. No.: WO03/015700

PCT Pub. Date: Feb. 27, 2003

(65) Prior Publication Data

US 2004/0236153 A1 Nov. 25, 2004

Related U.S. Application Data

(60) Provisional application No. 60/312,674, filed on Aug. 15, 2001.

(51) Int. Cl.
*A61K 31/075* (2006.01)
*C07C 43/205* (2006.01)

(52) U.S. Cl. .............. 514/715; 514/719; 514/720; 514/721; 568/644; 568/645; 568/646

(58) Field of Classification Search ............ 514/715, 514/719, 720, 721; 568/643, 644, 645, 646
See application file for complete search history.

(56) References Cited

U.S. PATENT DOCUMENTS

| | | | |
|---|---|---|---|
| 2,304,669 A * | 12/1942 | Adams .................... | 568/743 |
| 3,919,322 A | 11/1975 | Brossi et al. | |
| 4,025,516 A | 5/1977 | Razdan et al. | |
| 4,978,332 A * | 12/1990 | Luck et al. ............... | 604/19 |
| 5,227,537 A | 7/1993 | Stoss et al. | |
| 5,296,466 A * | 3/1994 | Kilbourn et al. ......... | 514/6 |
| 5,342,971 A | 8/1994 | Herlt et al. | |
| 5,747,524 A | 5/1998 | Cullinan et al. | |
| 5,939,429 A | 8/1999 | Kunos et al. | |
| 6,274,635 B1 * | 8/2001 | Travis .................... | 514/718 |
| 6,563,009 B1 * | 5/2003 | Kunos et al. ............ | 568/743 |

FOREIGN PATENT DOCUMENTS

WO    WO 99/53917 A1    10/1999
WO    WO 01/03690 A1    1/2001

OTHER PUBLICATIONS

Bukoski et al., "$CD_1$ Receptor Antagonist SR141716A Inhibits $Ca^{2+}$-Induced Relaxation in $CB_1$ Receptor-Deficient Mice," *Hypertension* 39:251-257 (2002).
Childers et al., "A Novel Approach to the Synthesis of the Cannabinoids," *J. Org. Chem.* 49:5276-5277 (1984).
Consroe et al., "Antiepileptic Potential of Cannabidiol Analogs," *J. Clin. Pharmacol.* 21:428S-436S (1981).
Ferraro et al., "The Cannabinoid Receptor Agonist WIN 55,212-2 Regulates Glutamate Transmission in Rat Cerebral Cortex: an In Vivo and In Vitro Study," *Cereb. Cortex* 11:728-733 (2001).
Járai et al., "Cannabinoid-Induced Mesenteric Vasodilation Through an Endothelial Site Distinct from CB1 OR CB2 Receptors," *PNAS* 96:14136-14141 (1999).
Korte et al., "Chemical Classification of Plants, XXIX. Hashish, 8, Synthesis of DL-Cannabidiol and its Methyl Homologs," *Justus Liebigs Annalen der Chemie* 693:165-170 (1966).

(Continued)

*Primary Examiner*—Rosalynd Keys
(74) *Attorney, Agent, or Firm*—Klarquist Sparkman LLP (57) ABSTRACT

Methods and compounds for reversing pathological vasodilation of blood vessels, for example vasodilation caused by activation of CB1-like receptors, by administering to a subject a therapeutically effective amount of a compound sufficient to induce vasoconstriction, the compound comprising:

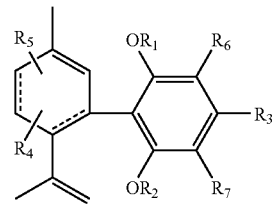

wherein dashed lines independently represent either a single or a double bond, $R_1$ is a lower alkyl, $R_2$ is a lower alkyl, $R_3$ is a lower alkyl or halogen, $R_4$ is a lower alkyl or hydrogen, $R_5$ is a lower alkyl or hydrogen, $R_6$ is a hydrogen, lower alkyl or halogen, and $R_7$ is a hydrogen, lower alkyl or halogen. The vasoconstrictor can be used for a variety of purposes, including hemostasis or the treatment of shock, for example vasodilatory shock syndromes such as septic shock.

24 Claims, 5 Drawing Sheets

OTHER PUBLICATIONS

Martin et al., "Structure-Anticonvulsant Activity Relationships of Cannabidiol Analogs," *NIDA Research Monograph* 79:48-58 (1987).

Srebnik et al., "Base-Catalysed Double-Bond Isomerizations of Cannabinoids: Structural and Stereochemical Aspects," *J. Chem. Soc. Perkin Trans.* __:2881-2886 (1984).

Varga et al., "Platelet- and Macrophage-Derived Endogenous Cannabinoids are Involved in Endotoxin-Induced Hypotension," *FASEB J.* 12:1035-1044 (1998).

Chemical Abstracts, 65:7221e.

Burstein et al., "Prostaglandins and Cannabis XV. Comparison of Enantiomeric Cannabinoids in Stimulating Prostaglandin Synthesis in Fibroblasts," Life Sciences, 39(19):1813-1823 (1986).

Mechoulam et al., "Enantiomeric Cannabinoids: Stereospecificity of Psychotropic Activity," Experientia, 44:762-764 (1988).

Thakur et al., "Enantiomeric Resolution of a Novel Chiral Cannabinoid Receptor Ligand," J. Biochem. Biophys. Methods, 54:415-422 (2002).

* cited by examiner

Figure 1. Changes in mean blood pressure (MAP) in response to LPS (100 μg/kg i.v.) in untreated (open circles) and SR141716A-pretreated (3 mg/kg i.v.) anesthetized control mice (top), CB1 knockout mice (middle) and CB1/CB2 double knockout mice (bottom)

Figure 2. Vasodilator response of rat isolated mesenteric branch arteries to Abn-cbd alone (open circles) or in the presence of different concentrations of O-1918. Arteries were mounted in a wire myograph as described and precontracted with phenylephrine. Relaxation is expressed as % of the phenylephrine-induced vasoconstrictor tone, 0% representing maximal relaxation. Note that O-1918 causes concentration-dependent inhibition of the relaxing effect of Abn-cbd, as indicated by the progressive right-shift of the concentration-response curve.

Fig. 4

VASOCONSTRICTOR CANNABINOID ANALOGS

CROSS REFERENCE TO RELATED APPLICATION

This is the U.S. National Stage of International Application No. PCT/US02/26050, filed Aug. 14, 2002 (published in English under PCT Article 21(2)), which in turn claims the benefit of U.S. provisional patent application No. 60/312,674 filed, Aug. 15, 2001, which is also incorporated herein by reference.

FIELD OF THE DISCLOSURE

The present disclosure concerns pharmaceutical compounds and compositions that are useful as vasoconstrictors, and the use of these compounds, for example in the treatment of shock.

BACKGROUND OF THE DISCLOSURE

Shock is a condition in which blood perfusion of peripheral tissues is inadequate to sustain normal tissue metabolism. The fundamental defect in this condition is usually hypotension, so that oxygen delivery or uptake is inadequate for aerobic metabolism. This defect results in a shift to anaerobic metabolism, with increased production and accumulation of lactic acid. When shock persists, impaired organ function is followed by irreversible cell damage and death.

The major causes of shock are hypovolemic shock (often from acute hemorrhage), cardiogenic shock (for example from arrhythmia or heart failure), and vasodilatory shock (caused by vascular dilation, as seen for example in cerebral trauma, drug intoxication, heat exposure, or septic shock accompanying a gram negative bacterial infection). The symptoms and signs of shock are well known to the clinician, and include lethargy, confusion, cold extremities that are often moist and cyanotic, prolonged capillary filling time, a weak and rapid pulse, and (ultimately) profound hypotension.

Septic shock is a type of vasodilatory shock that is often accompanied by a clinical presentation that suggests infection, such as fever, chills, warm, flushed skin, and hemodynamic instability (characterized by a falling and rising blood pressure). Septic shock is an often fatal condition that accompanies severe microbial infections, frequently with gram-negative bacteria such as *Escherichia coli*, *Pseudomonas aeruginosa* and *Klebsiella* or *Bacteroides* species. Gram-positive bacterial infections can also lead to septic shock, particularly those infections caused by *Staphylococcus aureus* and the *Pneumococcus*. The bacterial infections can be acquired by routes such as ingestion, personal contact, or trauma, but infections are often nosocornial consequences of therapeutic procedures, including implantation of indwelling catheters or prosthetic devices. Septic shock often occurs in immunocompromised subjects, and therefore has been an increasing problem in recent years because of the increasing number of individuals who are immunocompromised. For example, subjects with HIV disease or who are taking immunosuppressive drugs for the treatment of cancer or organ transplantation rejection are at increased risk of developing septic shock.

In view of the above, there exists a need for agents that counteract the vasodilation associated with shock.

SUMMARY OF THE DISCLOSURE

The present inventors have demonstrated that abnormal cannabidiol (Abn-cbd) is a selective agonist and cannabidiol is a selective antagonist of an as yet unidentified cannabinoid-like or non-classical receptor distinct from the known cannabinoid receptors CB1 and CB2. Agonists of these receptors, such as Abn-cbd, are believed to cause vasodilation. Even cannabidiol itself, which is generally an antagonist of the putative receptor, has been found to cause some vasodilation, and it therefore acts as a partial agonist, or mixed agonist/antagonist. It would therefore be desirable to have an agent that acts as a pure, or substantially pure, antagonist at the CB1-like receptor. Such an agent would be particularly useful in the treatment of diseases in which hypotension is the result of the action of endogenous cannabinoids and drug-induced vasoconstriction is desirable, for example in hypotensive states, such as shock. The antagonist would have particular application in vasodilatory shock states, such as septic shock, but it could also be used to achieve selective hemostasis to stop bleeding induced by trauma or surgery.

This disclosure identifies vasoconstrictor compounds. Although not wishing to be bound by theory, it is believed that these compounds are substantially pure antagonists of the CB1-like receptor. In certain examples, the compound has the chemical structure wherein dashed lines independently represent either a single or a double bond;
  $R_1$ is a lower alkyl;
  $R_2$ is a lower alkyl;
  $R_3$ is halogen or a lower alkyl having 1 to 3 carbons;
  $R_4$ is a lower alkyl or hydrogen;
  $R_5$ is a lower alkyl or hydrogen;
  $R_6$ is a hydrogen, lower alkyl or halogen; and
  $R_7$ is a hydrogen, lower alkyl or halogen.

Alternatively, the compound has the chemical structure wherein dashed lines independently represent either a single or a double bond;
  $R_1$ is a lower alkyl (such as methyl or propyl, for example isopropyl);
  $R_2$ is a lower alkyl (such as methyl or propyl, for example isopropyl);

$R_3$ is a halogen or a lower alkyl having 1 to 3 carbons (such as methyl);

$R_4$ is a lower alkyl or hydrogen (and in particular examples is hydrogen); and $R_5$ is a lower alkyl or hydrogen (and in particular examples is hydrogen).

In more specific examples, the compound has the chemical structure wherein $R_1$ is a lower alkyl;

$R_2$ is a lower alkyl; and $R_3$ is a halogen or lower alkyl having 1 to 3 carbons.

In even more specific examples, the compound has the chemical structure:

wherein $R_1$ is a methyl or propyl;

$R_2$ is a methyl or propyl; and $R_3$ is a methyl.

In particular examples, the compound is identified as compound O-1918:

In yet other embodiments, the present disclosure concerns a method of inducing vasoconstriction, for example by reversing pathological vasodilation, by administering to a subject a therapeutically effective amount of a compound sufficient to induce vasoconstriction, where the compound has the chemical structure:

wherein dashed lines independently represent either a single or a double bond, $R_1$, $R_2$ are independently a lower alkyl; $R_3$ and $R_4$ and are independently a lower alkyl or halogen; $R_5$ is a lower alkyl or hydrogen; and $R_6$ and $R_7$ are independently a hydrogen, lower alkyl or halogen.

In particular examples of the method, the administered agent is:

and in particular embodiments $R_4$ and $R_5$ are hydrogen, $R_1$ is a lower alkyl, $R_2$ is a lower alkyl, and $R_3$ is a halogen or lower alkyl. In even more particular examples, $R_3$ is methyl, and/or $R_1$, $R_2$ and $R_3$ are methyl.

The compound can be used in any clinical or laboratory situation in which reversal of vasodilation, such as vasodilation caused by an action of endogenous cannabinoids at CB1-like receptors is desired, for example in laboratory preparations (such as drug screening assays), or for inducing therapeutic (including diagnostic) vasoconstriction. There is a wide spectrum of therapeutic uses, such as inducing vasoconstriction (and therefore inhibiting blood flow) following traumatic or surgical injury. The method can also be applied to treat shock or other hemodynamic instabilities, for example vasodilatory shock conditions, such as septic shock (which can include lipopolysaccharide (LPS) induced shock) or hemorrhagic shock.

In yet other embodiments, any of the foregoing compounds may be incorporated into a pharmaceutical composition that includes a therapeutically effective amount of the compound and a pharmaceutical carrier.

DETAILED DESCRIPTION

I. Abbreviations
2-AG 2-arachidonyl glyceride
Abn-cbd abnormal cannabidiol
anandamide arachidonyl ethanolamide
CB1 Cannabinoid receptor 1
CB2 Cannabinoid receptor 2
L-NAME NG-nitro-L-argirie methyl ester
LPS lipopolysaccharide
NO nitric oxide II. Terms Unless otherwise noted, technical terms are used according to conventional usage. All chemical compounds include both the (+) and (−) stereoisomers, as well as either the (+) or (−) stereoisomer. Other chemistry terms herein are used according to conventional usage in the art, as exemplified by *The McGraw-Hill Dictionary of Chemical Terms* (1985) and *The Condensed Chemical Dictionary* (1981).

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. "Comprising" means "including." Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

As used herein, the term "Abnormal cannabidiol" (Abn-cbd), refers to a selective agonist of an as-yet unidentified cannabinoid-like or non-classical receptor distinct from CB1 or CB2 receptors. Agonists of these receptors, such as Abn-cbd, are believed to cause vasodilation.

Abn-cbd does not bind to the brain cannabinoid (CB1) receptor and does not elicit cannabinoid-like neurobehavioral effects in rats and mice. However, Abn-cbd has been found to lower blood pressure and to dilate isolated mesenteric arteries in normal rats and mice, and also in genetically altered mice that do not express CB1 receptors (CB1 knockout mice), or mice that do not express either the CB1 or the CB2 receptor (CB1/CB2 double knockout mice). (*Proceedings of the National Academy of Sciences [PNAS]*, vol. 96, pp. 1413–1414 (1999), which is herein incorporated by reference.). Furthermore, cannabidiol (the parent compound of Abn-cbd), which is also devoid of neurobehavioral effects and does not bind to CB1 receptors, does not elicit mesenteric vasodilation but is able to antagonize the vasodilator effect of Abn-cbd (Id. and U.S. Pat. No. 5,939,429)

The vasodilator response to Abn-cbd remains unchanged in the presence of 100 µM NG-nitro-L-arginine methyl ester (L-NAME) and 10 µM indomethacin, which indicates that endothelial nitric oxide (NO) and cyclooxygenase products (such as prostacyclin) do not contribute to the response. Furthermore, in the presence of 5 µM capsazepine (Kd at vanilloid VR1 receptors: 285 nM), the bolus injection of 4 mg Abn-cbd elicited the same long lasting vasodilation as in its absence. This observation further indicates that inhibition of vasodilation by the Abn-cbd is not attributable to non-specific blockade of vanilloid receptors.

The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isopropyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to five carbon atoms. This term is further exemplified by such radicals as methyl, ethyl, n-propyl, i-propyl, n-butyl, t-butyl, i-butyl (or 2-methylpropyl), cyclopropylmethyl, i-amyl, and n-amyl. Lower alkyl groups can also be unsubstituted or substituted, where a specific example of a substituted alkyl is 1,1-dimethyl propyl. Particular examples of lower alkyls are methyl, butyl and propyl (including isopropyl).

The term "alkoxy" refers to a substituted or unsubstituted alkoxy, where an alkoxy has the structure —O—R, where R is substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent. "Lower alkoxy" refers to any alkoxy in which R is a lower alkyl. Particular examples of alkoxys include methoxy, ethoxy and propoxy groups.

As used herein, a "cannabinoid" is a chemical compound (such as cannabinol, THC or cannabidiol) that is found in the plant species *Cannabis sativa* (marijuana), and metabolites and synthetic analogues thereof that may or may not have psychoactive properties. Cannabinoids therefore include (without limitation) compounds (such as THC) that have high affinity for the cannabinoid receptor (for example $K_i$<250 nM), and structurally related compounds that do not have significant affinity for the cannabinoid receptor (such as cannabidiol, CBD). Cannabinoids also include compounds that have a characteristic dibenzopyran ring structure (of the type seen in THC) and cannabinoids that do not possess a pyran ring (such as cannabidiol). Many other cannabinoids are disclosed in Agurell et al., *Pharmacol. Rev.* 38:31–43, 1986, which is incorporated by reference.

Naturally occurring cannabinoids include both plant-derived cannabinoids and endogenous cannabinoids that occur naturally in mammals. Plant-derived cannabinoids are known to elicit dramatic psychobehavioral effects and also have complex cardiovascular activity, a prominent component of which is hypotension (Vollmer et al. *J. Pharm. Pharmacol.* 1974, 26:186–198). Endogenous cannabinoids (endocannabinoids) are a class of lipid-like molecules that share receptor binding sites with plant-derived cannabinoids, and mimic many of their neurobehavioral effects.

Two endocannabinoids that have been characterized in some detail are arachidonyl ethanolamide (anandamide) (Devane et al. *Science* 1992, 258:1946–1949; Felder et al. *Proc. Natl. Acad. Sci. USA.* 1993, 90:7656–7660) and 2-arachidonyl glyceride (2-AG) (Mechoulam et al. *Biochem. Pharmacol.* 1995, 50:83–90). Like plant-derived cannabinoids, both anandamide and 2-AG are capable of eliciting hypotension (Varga et al. *FASEB J.* 1998, 12:1035–1044; Varga et al. *Eur. J. Pharmacol.* 1995, 278:279–283; Stein et al. *Br. J. Pharmacol.* 1996, 119:107–114; Varga et al. *Hypertension* 1996, 28:682–688; Lake et al. *Hypertension* 1997, 29:1204–1210; Calignano et al. *Eur. J. Pharmacol.* 1997, 337: R1–R2; Járai et al., *Hypertension* 2000, 35:679–684).

Cannabinoid receptors: Cannabinoids exert their effects by binding to specific receptors located in the cell membrane. Two cannabinoid receptors have been cloned, and include the CB1 receptor expressed primarily in the brain (Matsuda et al. *Nature* 1990, 46:561–564) but also in some peripheral tissues (Shire et al. *J. Biol. Chem.* 1995, 270: 3726–3731), and CB2 receptors expressed by cells of the immune system (Munro et al. *Nature* 1993, 365:61–65). Studies with the selective CB1 receptor antagonist SR141716A have implicated the CB1 receptor subtype in cannabinoid-induced hypotension and bradycardia (Varga et al., *Eur. J. Pharmacol.* 1995, 278:279–283; Lake et al., *J. Pharmacol. Exp. Ther.* 1997, 281:1030–1037), a conclusion recently confirmed by the use of mice deficient in CB1 receptors (Ledent et al., *Science* 1999, 283:401–404).

The term "halogen" refers to fluoro, bromo, chloro and iodo substituents.

A "mammal" includes both human and non-human mammals. Similarly, the term "subject" includes both human and veterinary subjects. An animal is a living multicellular vertebrate organism, a category which includes, for example, mammals and birds.

A "pharmaceutical agent" or "drug" refers to a chemical compound or other composition (including peptide based pharmaceuticals) capable of inducing a desired therapeutic or prophylactic effect when properly administered to a subject.

As referred to herein, the term "psychoactivity" means "cannabinoid receptor mediated psychoactivity." Such effects include euphoria, lightheadedness, reduced motor coordination, and memory impairment. Psychoactivity is not meant to include non-cannabinoid receptor mediated effects such as the anxiolytic effect of CBD.

"SR141716A" is a selective CB1 receptor antagonist.

"Substantially pure antagonist" refers to an agent that acts almost purely as an antagonist at a receptor. For example, an agent that is a substantially pure antagonist of the CB1-like receptor will a) not affect blood vessel diameter by itself (i.e. will not dilate or constrict blood vessels) across the doses in which the agent would be therapeutically used, but b) will be able to prevent the vasodilator effect of a subsequently administered (or released) agonist for the same receptor. Alternatively, if the agonist is administered (or released) first to cause vasodilation, the antagonist will reverse this vasodilation, which means that it will constrict the blood vessel previously dilated by the agonist. A "selective" CB1-like antagonist is an agent that will inhibit or reverse the vasodilation caused by a CB1-like receptor agonist, but not the vasodilation caused by agonists acting at other receptors that mediate vasodilation, such as acetylcholine receptors.

"Therapeutic" is a generic term that includes both diagnosis and treatment. Hence, therapeutic uses of the vasoconstrictor could include diagnostic tests (such as vasoconstriction in a myocardial stress test) as well as administration for the inhibition, reversal or prevention of pathological conditions.

III. Detailed Description of Several Embodiments

This disclosure identifies vasoconstrictor compounds. In certain examples, the compound has the chemical structure:

wherein dashed lines independently represent either a single or a double bond;
$R_1$ is a lower alkyl;
$R_2$ is a lower alkyl;
$R_3$ is halogen or a lower alkyl having 1 to 3 carbons;
$R_4$ is a lower alkyl or hydrogen;
$R_5$ is a lower alkyl or hydrogen;
$R_6$ is a hydrogen, lower alkyl or halogen; and
$R_7$ is a hydrogen, lower alkyl or halogen.

Alternatively, in some embodiments the compound has the chemical structure:

wherein dashed lines independently represent either a single or a double bond;
$R_1$ is a lower alkyl (such as methyl or propyl, for example isopropyl);
$R_2$ is a lower alkyl (such as methyl or propyl, for example isopropyl);
$R_3$ is a halogen or a lower alkyl having 1 to 3 carbons (such as methyl);
$R_4$ is a lower alkyl or hydrogen (and in particular examples is hydrogen); and
$R_5$ is a lower alkyl or hydrogen (and in particular examples is hydrogen).

In more specific examples, the compound has the chemical structure:

wherein $R_1$ is a lower alkyl;
$R_2$ is a lower alkyl; and
$R_3$ is a halogen or lower alkyl having 1 to 3 carbons.

In even more specific examples, the compound has the chemical structure:

wherein $R_1$ is a methyl or propyl;
$R_2$ is a methyl or propyl; and
$R_3$ is a methyl.

In even more particular examples, the compound is a compound identified as compound O-1918:

In yet other embodiments, the present disclosure concerns a method of inducing vasoconstriction, for example by reversing pathological vasodilation, by administering to a subject a therapeutically effective amount of a compound sufficient to induce vasoconstriction, where the compound has the chemical structure:

wherein dashed lines independently represent either a single or a double bond, $R_1$ and $R_2$ are independently lower alkyls; $R_3$ and $R_4$ and are independently a lower alkyl or halogen; $R_5$ is a lower alkyl or hydrogen; and $R_6$ and $R_7$ are independently a hydrogen, lower alkyl or halogen.

In particular examples of the method, the administered agent is:

and in particular embodiments, $R_4$ and $R_5$ are hydrogen, $R_1$ is a lower alkyl, $R_2$ is a lower alkyl, and $R_3$ is a halogen or lower alkyl. In even more particular examples, $R_3$ is methyl, and/or $R_1$, $R_2$ and $R_3$ are methyl.

In certain embodiments, the method includes administering the compound to a subject experiencing or at risk for experiencing shock, and in particular examples, the shock is vasodilatory or septic shock. In certain examples, the method is a method of vasoconstricting blood vessels that are dilated by the activation of a CB1-like receptor.

In yet other embodiments, any of the foregoing compounds may be incorporated into a pharmaceutical composition that includes a therapeutically effective amount of the compound and a pharmaceutical carrier.

In still other embodiments, any of the foregoing compounds is incorporated into a kit. Optionally, the kit may include one or more other vasoconstrictive or inotropic, or antibiotic drugs. In particular examples, the vasoconstrictive or inotropic drug is norepinephrine, dopamine, or dobutamine.

A. Synthesis of Vasoconstrictor Cannabinoid Analogs

The novel vasoconstrictor cannabinoid analog, O-1918, is synthesized using standard laboratory techniques. Briefly, O-1918 was synthesized by adding dry potassium carbonate to a Wheaton-type pressure tube, followed by a solution of (–)-4-(3,3,4trans-p-menthadien-1,8)-yl-resorcinol (O-1602) in dry acetonitrile. Additional acetonitrile was used as washings, which were transferred to the pressure tube. Subsequently, iodomethane was added and the mixture was stirred and heated to 70–80° C. in an oil bath for 16 hours. After cooling, the mixture was filtered and washed with fresh acetonitrile. The filtrate was concentrated on a rotary evaporator and the residue was dissolved in ether. The ether solution was washed with HCl and three times with water, then dried and concentrated on the rotary evaporator. It was purified by flash chromatography. The fractions containing the material were monitored by TLC, visualized by phosphomolybdic acid or iodine, and concentrated. $^1$HNMR showed appropriate peaks.

In general, to synthesize other analogs within the scope of the claim, the appropriate resorcinol is condensed with p-mentha-2,8-dien-1-ol with a mild acid as a catalyst and subjected to reflux for approximately four hours (Razdan et al., J. Am. Chem. Soc 1974, 96:5860–5865; T. Pstrzieka et al., *Helv. Chimica Acta* 1969, 52:1102). Purity is established by nuclear magnetic resonance spectroscopy, gas chromatography, and elemental analysis.

To make the alkoxy homologs, the same procedure is used as in the synthesis of O-1918 (see above) except that the appropriate alkyl halide is used in place of iodomethane. For example, to prepare the propoxy instead of the methoxy, iodopropane is used instead of iodomethane.

Substituents $R_4$ and $R_5$ (see below) are added to the compound by choosing or synthesizing the starting compound with the desired substituents on it. This starting compound is a terpene made from pinene, which is a naturally occurring material.

B. Identification of Analogs

The identification of the substantially pure antagonist of the non-classical cannabinoid receptor now permits one to screen for additional analogs of this agent that have similar activity. The binding of the O-1918 ligand to the receptor can be used to isolate and characterize the receptor, for example by labeling the O-1918 ligand with a detectable label that can be used to detect the receptor. Moreover, the labeled ligand can also be used in competitive displacement assays to test (or screen for) additional compounds that bind to this receptor. The activity of any analogs of the disclosed compounds to antagonize Abn-cbd-induced vasorelaxation can be determined using isolated blood vessels set up in a wire myograph, as in Example 2, below.

The putative non-classical cannabinoid receptor for which Abn-cbd is an agonist and O-1918 is an antagonist is coupled to Gi or Go and activates PKB/akt. Therefore, in addition to the biophysical measurements outlined in Example 2, phosphorylation of PKB/akt can be used to screen for other ligands of the as-yet unidentified receptor. For example, vascular smooth muscle cells are isolated from mouse mesenteric arteries by dissection and enzymatic dissociation, or other endothelial cells such as HUVEC could be used. Cells are plated in 24well plates and grown to confluency. Experimental wells are pre-treated for ten minutes with 10-nM–100 µM O-1918, or other candidate ligand. Cells are then incubated for 1 hour in culture medium containing 10 nM–100 µM Abn-cbd. Cellular reactions are halted by the addition of 0.5 ml ice-cold lysing buffer, and PKB/akt phosphorylation is quantified and visualized by Western immunoblotting, as described above.

C. Pharmaceutical Compositions

The compounds described herein may be formulated in a variety of ways depending on the location and type of disease to be treated. Pharmaceutical compositions are thus provided for both local use as well as for systemic use. Therefore, the disclosure includes within its scope pharmaceutical compositions comprising at least one vasoconstrictor cannabinoid analog formulated for use in human or veterinary medicine.

Pharmaceutical compositions that include at least one compound as described herein as an active ingredient, or that include both a vasoconstrictor cannabinoid analog and an additional vasoconstrictive or inotropic drug or antibiotic as active ingredients, may be formulated with an appropriate solid or liquid carrier, depending upon the particular mode of administration chosen. Additional active ingredients include, for example, norepinephrine, dopamine, or dobutamine.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutical compositions that comprise a vasoconstrictor cannabinoid analog, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

D. Therapeutic Uses

The present disclosure includes a treatment for septic shock in a subject such as an animal, for example a mammal, such as a laboratory animal or human subject. The method includes administering the compound of the present disclosure, or a combination of the compound and one or more other pharmaceutical agents, to the subject in a pharmaceutically compatible carrier and in an amount effective to inhibit the development or progression of septic shock. Although the treatment can be used prophylactically in any subject in a demographic group at significant risk for such diseases, subjects can also be selected using more specific criteria, such as a definitive diagnosis of the condition. For example, treatment can be initiated in a subject having signs and symptoms of shock, such as lethargy, somnolence, poor peripheral perfusion and hypotension or other hemodynamic instability. In particular examples, the clinical picture will suggest a cause for shock, such as an indwelling catheter in an immunocompromised person who is at risk of septicemia, and who may present classical signs of infection (such as fever and chills) with laboratory evidence of infection (leukocytosis with the appearance of blasts in peripheral blood samples).

The vehicle in which the drug is delivered can include pharmaceutically acceptable compositions of the drugs, using methods well known to those with skill in the art. Any of the common carriers, such as sterile saline or glucose solution, can be utilized with the drugs provided by the disclosure. Routes of administration include but are not limited to oral and parenteral routes, such as intravenous (iv), intraperitoneal (ip), rectal, topical, ophthalmic, nasal, and transdermal.

The drugs may be administered intravenously in any conventional medium for intravenous injection, such as an aqueous saline medium, or in blood plasma medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy* (19$^{th}$ Edition, 1995) in chapter 95.

Embodiments of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions.

Therapeutically effective doses of the compounds of the present disclosure can be determined by one of skill in the art, with a goal of achieving tissue concentrations that are at least as high as the IC$_{50}$ of each drug tested in the foregoing examples. An example of a dosage range is 0.1 to 200 mg/kg body weight orally in single or divided doses. Another example of a dosage range is 1.0 to 100 mg/kg body weight orally in single or divided doses. For oral administration, the compositions are, for example, provided in the form of a tablet containing 0.1 or 1.0 to 1000 mg of the active ingredient, particularly 1, 5, 10, 15, 20, 25, 50, 100, 200, 400, 500, 600, and 1000 mg of the active ingredient for the symptomatic adjustment of the dosage to the subject being treated.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy. For example, severe life-threatening and prolonged hypotension with multi-organ failure would be treated more aggressively than less severe clinical presentations. Clinical responses can be assessed by a variety of parameters, such as increased blood pressure in an otherwise hypotensive individual.

E. Kits

The compounds disclosed herein can be supplied in the form of kits for use in prevention and/or other treatment of a disorder, condition or diseases (e.g., septic shock). In such a kit, a clinically effective amount of one or more of the compounds or peptides is provided in one or more containers. The compounds or peptides may be provided suspended in an aqueous solution or as a freeze-dried or lyophilized powder, for instance. In certain embodiments, the compounds will be provided in the form of a pharmaceutical composition.

Kits according to this disclosure can also include instructions, usually written instructions, to assist the user in treating a disorder, condition or disease (e.g., treatment of hemorrhage or shock) with the vasoconstrictor. The instructions can be for use of the drug for any of the purposes described herein. Such instructions can optionally be provided on a computer readable medium.

The container(s) in which the compound(s) and/or peptide(s) are supplied can be any conventional container that is capable of holding the supplied form, for instance, microfuge tubes, ampoules, or bottles. In some applications, the therapeutic compound may be provided in pre-measured single use amounts in individual, typically disposable, tubes or equivalent containers.

The amount of a compound supplied in the kit can be any appropriate amount, depending for instance on the market to which the product is directed. For instance, if the kit is adapted for research or clinical use, the amount of each vasoconstrictor compound provided would likely be an amount sufficient for several treatments.

Certain kits according to this disclosure will also include one or more other agents useful in treating septic shock. For example, such kits may include one or more effective doses of other vasoconstrictive or inotropic drugs (such as norepinephrine, dopamine or dobutamine), or other agents useful in the treatment of particular conditions (such as an antibiotic in the treatment of septic shock).

The subject matter of the present disclosure is further illustrated by the following non-limiting Examples.

EXAMPLE 1

Synthesis of O-1918

The novel vasoconstrictor cannabinoid analog, O-1918, was synthesized in the following manner. Potassium carbonate and acetonitrile were purchased from Sigma-Aldrich, Co. (St. Louis, Mo.). O-1602 was synthesized as described in International Patent Publication WO 01/03690, which is incorporated by reference in its entirety.

O-1918 was synthesized by adding 0.220 g (1.59 mmol) of dry potassium carbonate (−325 mesh) to a Wheaton-type pressure tube, followed by a solution of (−)-4-(3,3,4-trans-p-menthadien-1,8)-yl-resorcinol (O-1602; 0.090 g; 0.3483 mmol) in 2 ml of dry acetonitrile. An additional 1 ml of acetonitrile was used as washings, which were transferred to the pressure tube. The mixture turned purple. Subsequently, 4 ml of iodomethane was added and the mixture was stirred and heated to 70–80° C. in an oil bath for 16 hours. After cooling, the mixture was filtered and washed with fresh acetonitrile. The filtrate was concentrated on a rotary evaporator and the residue was dissolved in ether. The ether solution was washed once with 10 ml of 1N HCl and three times with 10 ml of water, then dried and concentrated on the rotary evaporator to leave a gum of 0.090 g. It was purified by flash chromatography using 10 g of SiO$_2$ in hexane and eluting with first 1% and then 1.5% ethyl acetate/hexane mixture and collected in 10 ml fractions. The fractions containing the material were monitored by TLC (10% ethyl acetate/hexane), visualized by phosphomolybdic acid or iodine, and concentrated to give a gum of 0.076 g (77%). $^1$HNMR showed appropriate peaks; mass spectrum (M+1) 287; Anal. Calcd. For $C_{19}H_{26}O_2 \cdot 0.3H_2O$: C, 78.20; H, 9.19; Found: C, 78.40; H, 9.06.

In general, to synthesize other analogs within the scope of the claim, the appropriate resorcinol is condensed with compound 1 (p-mentha-2,8-dien-1-ol) with a mild acid as a catalyst and subjected to reflux for approximately four hours (Razdan et al., *J. Am. Chem. Soc* 1974, 96:5860–5865; T. Pstrzieka et al., *Helv. Chimica Acta* 1969, 52:1102). Purity is established by nuclear magnetic resonance spectroscopy, gas chromatography, and elemental analysis.

To make the alkoxy homologs, the same procedure is used as in the synthesis of O-1918 (see above) except that the appropriate alkyl halide is used in place of iodomethane. For example, to prepare the propoxy instead of the methoxy, iodopropane was used instead of iodomethane.

Substituents $R_4$ and $R_5$ can be added to the compound by choosing or synthesizing Compound 1 with the desired substituents on it. Compound 1 is a terpene made from pinene, which is a naturally occurring material.

EXAMPLE 2

Effects of O-1918 on Mouse Blood Pressure

This example illustrates that O-1918 blocks an as-yet unidentified, non-classical (non CB1/CB2) cannabinoid receptor.

The endogenous cannabinoid anandamide causes vasodilation in the perfused mesenteric vascular bed of genetically modified mice that lack CB1 or both CB1 and CB2 receptors (*Proc. Natl. Acad. Sci. USA*, 96: 14136–14141, 1999). In addition, a structurally-modified analog of the plant-derived cannabinoid, cannabidiol, called abnormal cannabidiol (Abn-cbd), does not bind to CB1 receptors, yet it causes hypotension and vasodilation in normal and CB1/CB2 deficient mice, indicating that it acts as a selective agonist for an as-yet unidentified, non-classical cannabinoid receptor (Ibid).

Figure 1A:
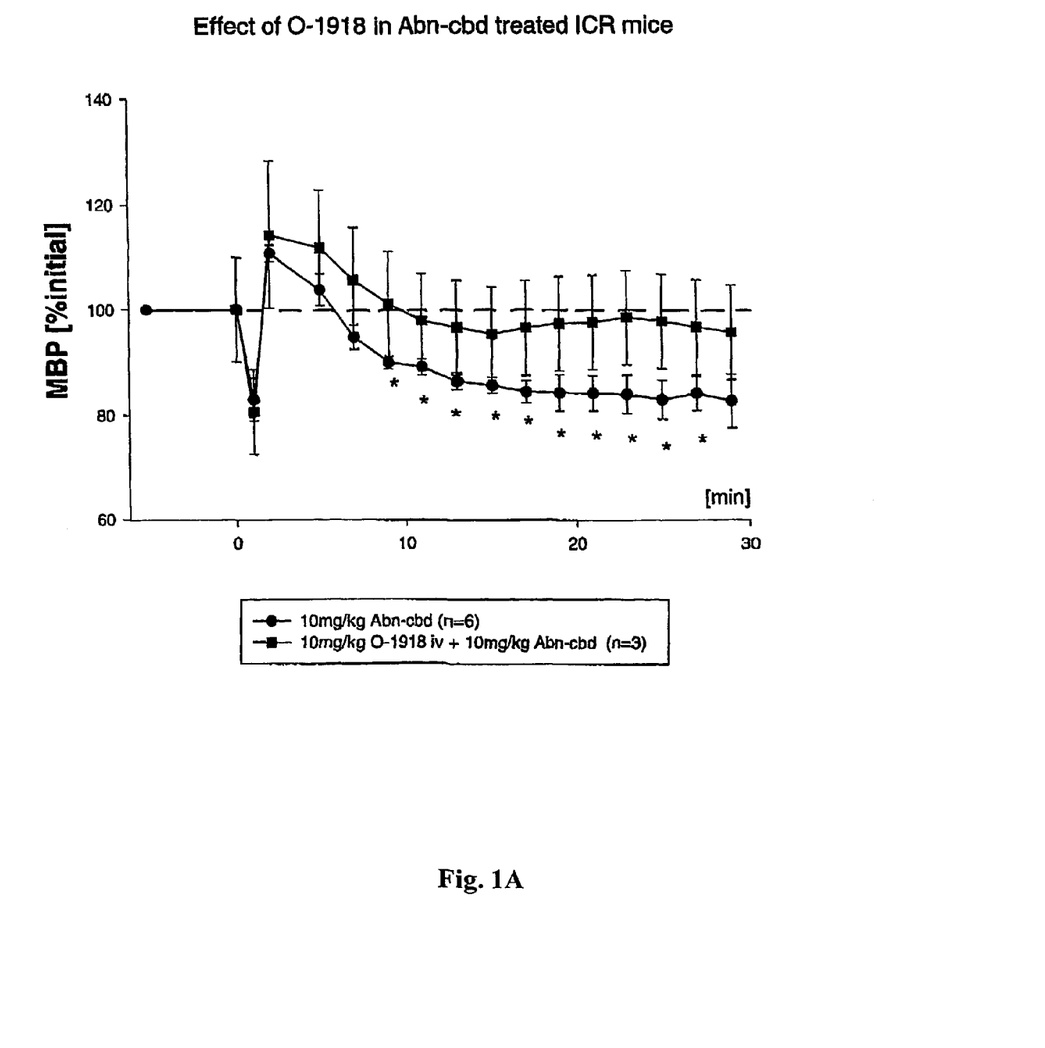
FIGS. 1A and 1B are graphs showing the effect of O-1918 on the mean arterial blood pressure of Abn-cbd -treated (FIG. 1A) and HU-210-treated (FIG. 1B) ICR mice.
Figure 1B:
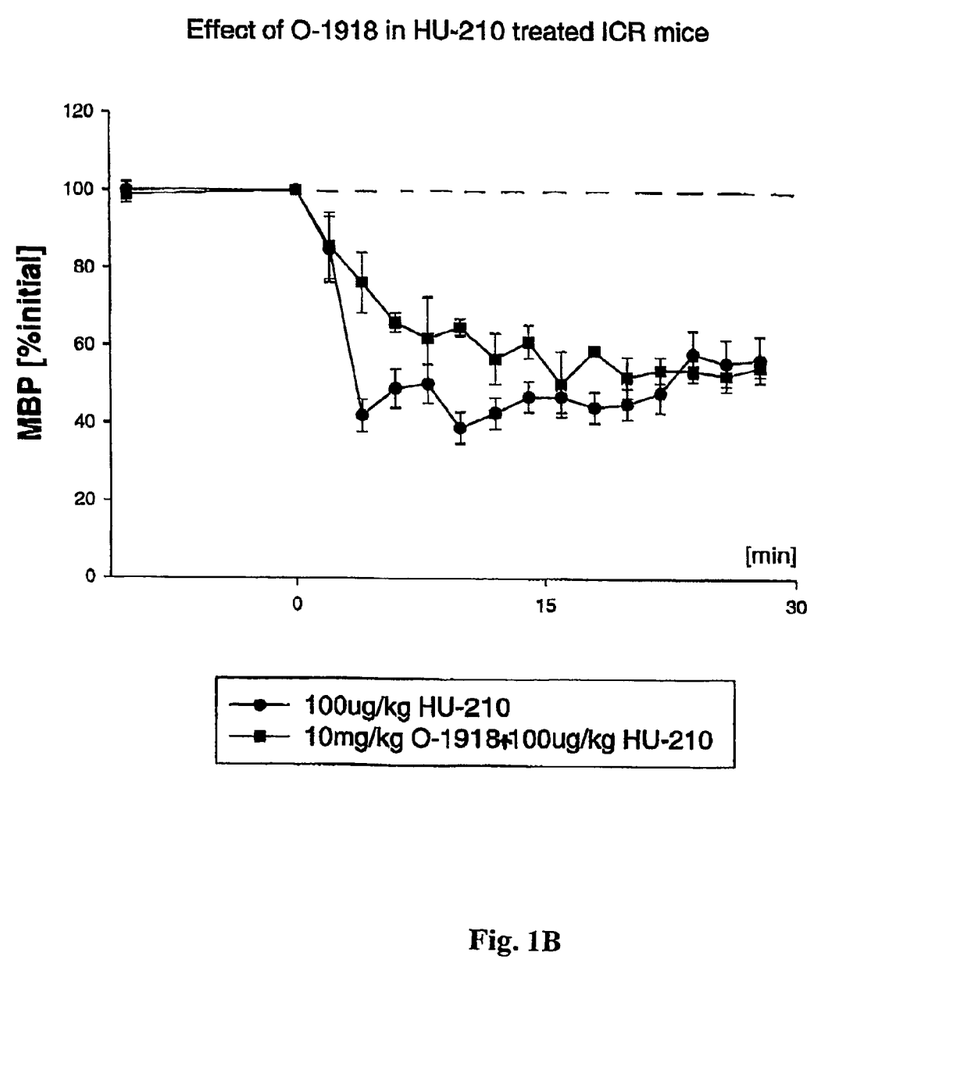

By way of example, ICR mice were anesthetized with pentobarbital, and polyethylene cannulae were inserted into the femoral artery and vein for monitoring blood pressure and injecting drugs, respectively. Blood pressure was monitored directly by connecting the arterial cannula to a pressure transducer and physiograph. Intravenous injection of 10 mg/kg Abn-cbd caused a transient drop in blood pressure followed by a brief increase and then a more prolonged, significant decrease in pressure. Other animals were first injected with 10 mg/kg O-1918, which did not influence blood pressure. However, when 10 mg/kg of Abn-cbd was injected 10 min following the injection of 10 mg/kg O-1918, the initial transient changes in blood pressure were present but the prolonged hypotensive phase of the effect of Abn-cbd was absent (FIG. 1A). In contrast, O-1918 did not antagonize the hypotensive effect of HU-210, a potent CB1/CB2 agonist (FIG. 1B) whose hypotensive effect is absent in CB1 receptor deficient mice (Jarai et al., *Proc. Natl. Acad. Sci. USA* 96:10136–14141, 1999). This indicates that O-1918 is a selective antagonist of the non-CB1/CB2 receptor that mediates the hypotensive action of Abn-cbd, and does not block CB1 receptors.

EXAMPLE 3

Effects of O-1918 on the Hypotension Induced by LPS

This example illustrates that O-1918 prevents the hypotension elicited by bacterial endotoxin, by inhibiting a non-CB1/CB2 receptor.

Figure 2:
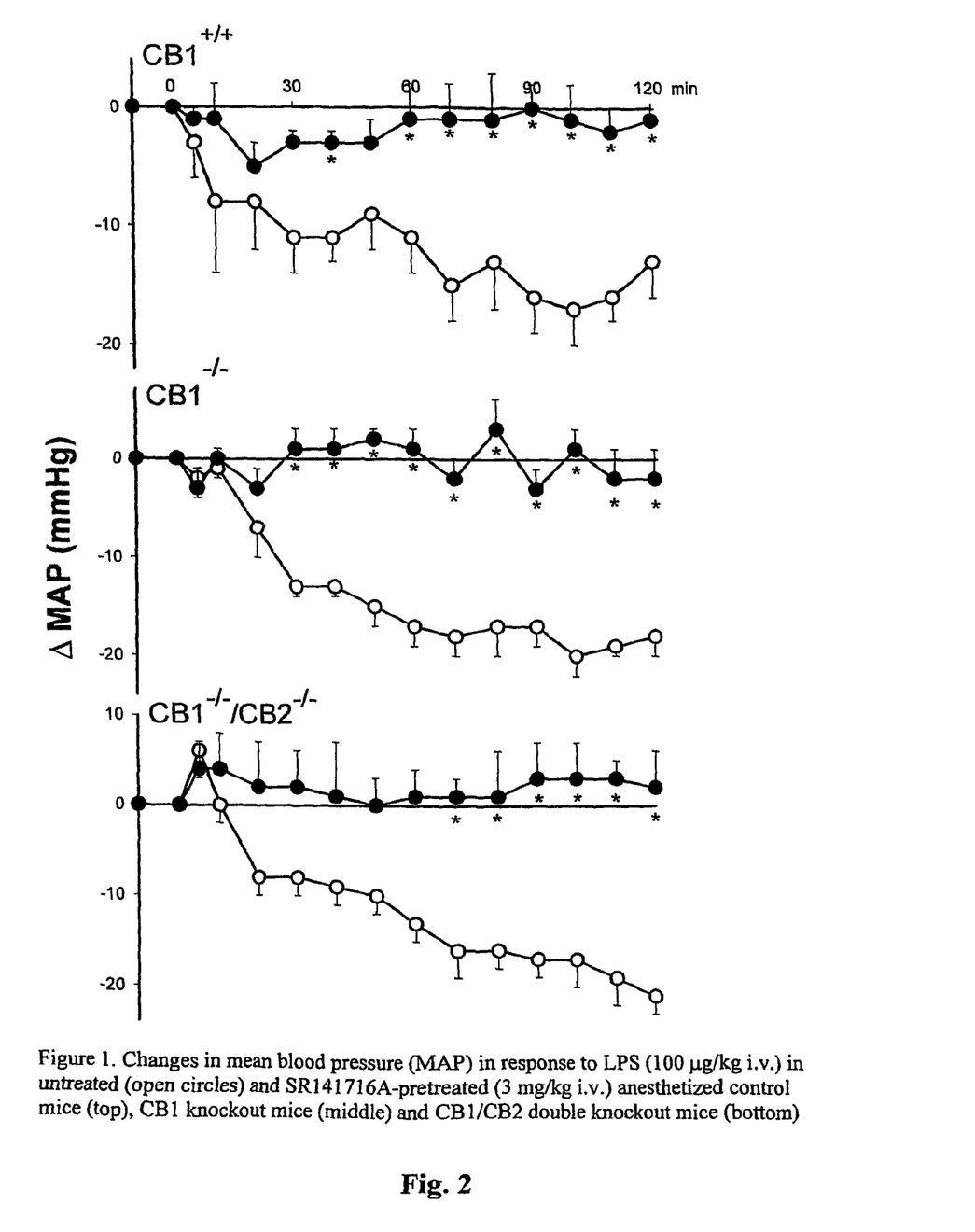
FIG. 2 is a graph that illustrates changes in mean arterial blood pressure (MAP) in response to LPS (100 μg/kg i.v.) in untreated (open circles) and SR141716A-pretreated (3 mg/kg i.v.) anesthetized control mice (top), CB1 knockout mice (middle) and CB1/CB2 double knockout mice (bottom).
Figure 3:
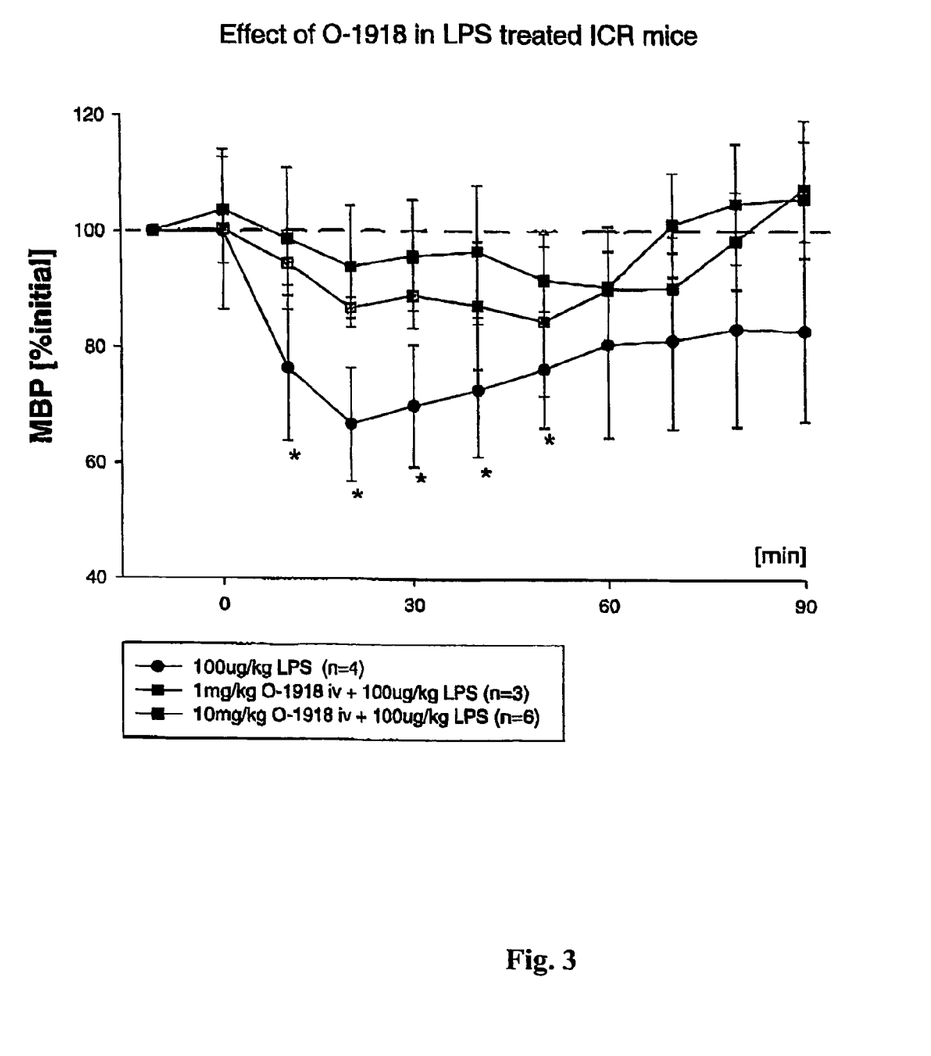
FIG. 3 is a graph that shows the effect of O-1918 on the mean arterial blood pressure of LPS-treated ICR mice.

The bacterial endotoxin, LPS, elicits hypotension in rats and mice that can be prevented by pretreatment of the animals with SR141716A (Varga et al., *FASEB J.* 12:1035–1044, 1998). SR141716A inhibits CB1 receptors, but it also inhibits CB1-like, non-classical cannabinoid receptors (Jarai et al., *Proc. Natl. Acad. Sci. USA*, 96:14136–14141, 1999). LPS causes hypotension, inhibited by pretreatment with 3 mg/kg SR141716A, in wild-type mice and also in mice deficient in CB1 or CB1 and CB2 receptors (FIG. 2). This indicates that most if not all of the LPS-induced hypotension is mediated by non-CB1/CB2 receptors. O-1918 is a putative antagonist of such receptors, and we tested whether O-1918 inhibits LPS-induced hypotension. Intravenous injection of pentobarbital-anesthetized ICR mice with 100 ng/kg LPS caused significant, long lasting hypotension, which was dose-dependently inhibited by pretreatment of the mice with 1 to 10 mg/kg O-1918 (FIG. 3).

EXAMPLE 4

Effects of O-1918 on Mouse Isolated Mesenteric Branch Arteries

This example illustrates that O-1918 antagonizes calcium-induced relaxation via inhibition of a non CB1/CB2 receptor.

Extracellular calcium causes vasodilation in rat and mouse mesenteric branch artery preparations, which depends on intact perivascular sensory nerves and is inhibited by SR141716A (Ishioka & Bukoski, *J. Pharmacol. Exp. Ther.* 289:245–250, 1999). This has been interpreted to suggest that extracellular calcium releases an endogenous cannabinoid, such as anandamide, from perivascular nerves, which would then dilate the vessels via either CB1 or "CB1-like" receptors. The vasodilator effect of extracellular calcium was tested in mesenteric branch arteries isolated from wild-type and CB1 receptor deficient mice, as described Bukoski et al., *Hypertension* 39:251–257, 2002). Arterial segments precontracted with 5 μM norepinephrine responded to the cumulative addition of extracellular calcium with a concentration-dependent relaxation that was similar in preparations from wild-type and CB1 receptor deficient mice. SR141716A caused concentration-dependent inhibition of calcium-induced relaxation in both wild-type and CB1 knockout mice. This suggests that the inhibition is mediated by non CB1 or "CB1-like" receptors. At a concentration of 10 μM, O-1918 also inhibited the calcium-induced relaxation in both wild-type and CB1 receptor deficient mice (Bukoski et al., *Hypertension* 39:251–257, 2002). This confirms the role of non-CB1/CB2 receptors in calcium-induced mesenteric vasodilation.

EXAMPLE 5

Effect of O-1918 on Rat Isolated Mesenteric Branch Arteries

The following example illustrates that O-1918 blocks an as-yet unidentified, non-classical (non CB1/CB2) cannabinoid receptor in the rat.

Figures 2, 4:
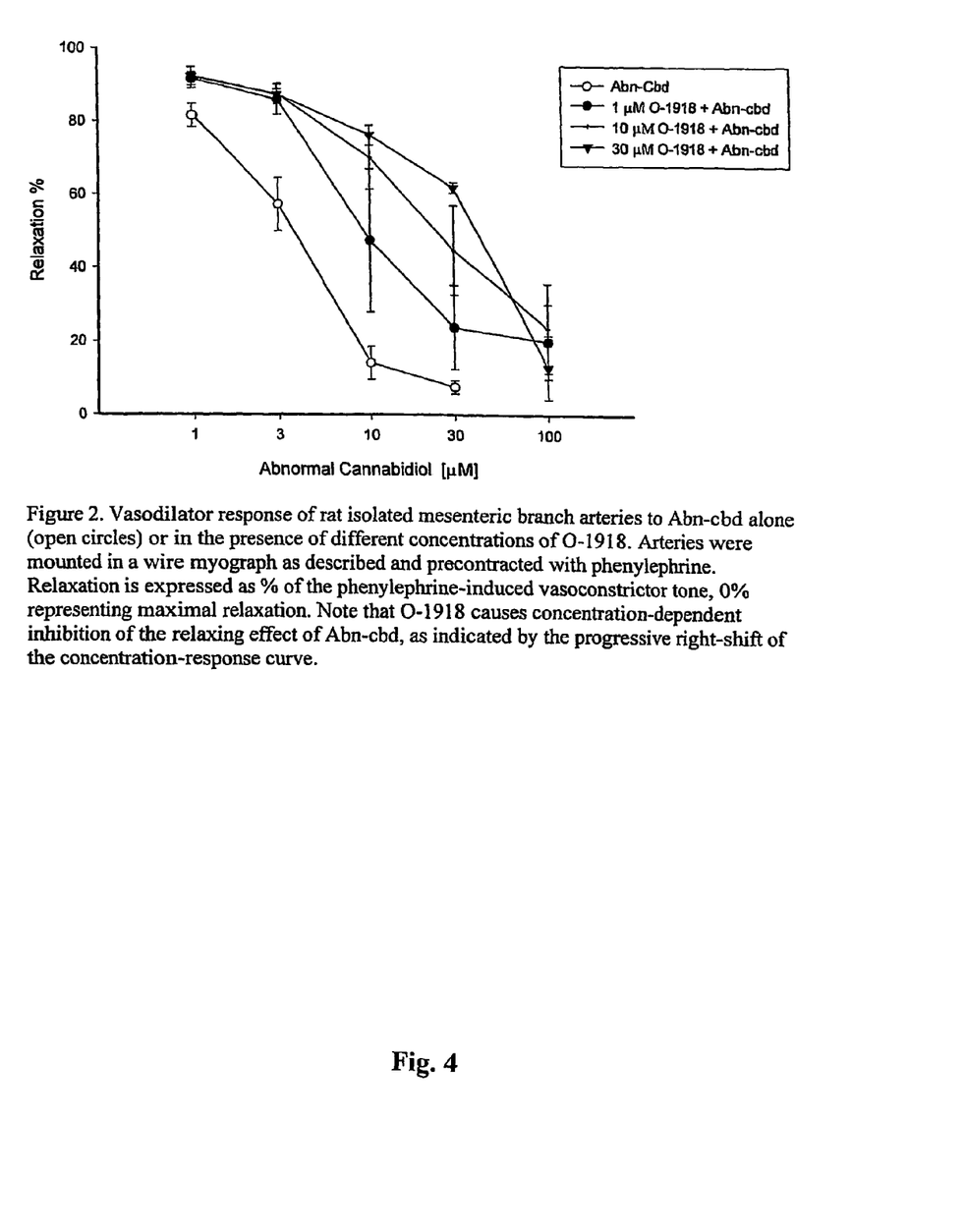
FIG. 4 is a graph that illustrates a vasodilator response of rat isolated mesenteric branch arteries to Abn-cbd alone (open circles), or in the presence of different concentrations of O-1918. Arteries were mounted in a wire myograph, and precontracted with phenylephrine. Relaxation is expressed as % of the phenylephrine-induced vasoconstrictor tone, 0% representing maximal relaxation. Note that O-1918 causes concentration-dependent inhibition of the relaxing effect of Abn-cbd, as indicated by the progressive right-shift of the concentration-response curve.

Rat isolated mesenteric branch arteries (~200 μm in diameter) were precontracted with phenylephrine and measurements were recorded with a wire myograph. Abnormal cannabidiol (Abn-cbd) acted as a full agonist to elicit concentration-dependent vasorelaxation ($EC_{50}$: 3.3±0.5 μM). O-1918 did not alter vascular tone at concentrations up to 30 μM. However, when preparations were preincubated with 1–10 μM O-1918, the dose-response curve to Abn-cbd was progressively right-shifted ($EC_{50}$ in the presence of 10 μM O-1918: 26±10 μM)(FIG. 4). Hence Abn-cbd is an agonist and O-1918 is a competitive antagonist at an endothelial receptor mediating vasorelaxation.

The specificity of this antagonism is indicated by the finding that 10 μM O-1918 did not inhibit the vasorelaxation caused by carbachol, an acetylcholine analog that acts at muscarinic receptors, or by CGRP, a vasodilator peptide that acts at CGRP receptors.

EXAMPLE 6

Administration of O-1918 to Mice to Reverse LPS Induced Hypotension

Endotoxin was used to induce hypotension in control mice as well as in mice deficient in CB1 or both CB1 and CB2 receptors. In all three groups of animals endotoxin (bacterial lipopolysaccharide or LPS, 100 μg/kg i.v.) was found to elicit hypotension, and in all three groups the hypotensive effect of LPS could be prevented by pretreatment of the animals with 3 mg/kg SR141716A (FIG. 1). These results indicate that endotoxin-induced ('septic') hypotension is mediated by CB1-like receptors rather than CB1 receptors. This possibility was further supported by successful treatment of normal anesthetized mice with 10 mg/kg O-1918, to prevent the hypotension that can be induced in these animals by the injection of 100 mg/kg LPS.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the following claims:

We claim:
1. A compound having the chemical structure:

wherein dashed lines independently represent either a single or a double bond;
$R_1$ is a lower alkyl;
$R_2$ is a lower alkyl;
$R_3$ is halogen or a lower alkyl having 1 to 3 carbons;
$R_4$ is a lower alkyl or hydrogen;
$R_5$ is a lower alkyl or hydrogen;
$R_6$ is a hydrogen, lower alkyl or halogen;
$R_7$ is a hydrogen, lower alkyl or halogen, and
wherein the compound is an enantiomerically pure (−) stereoisomer.

2. A compound having the chemical structure wherein dashed lines independently represent either a single or a double bond;
$R_1$ is a lower alkyl;
$R_2$ is a lower alkyl;
$R_3$ is a halogen or a lower alkyl having 1 to 3 carbons;
$R_4$ is a lower alkyl or hydrogen;
$R_5$ is a lower alkyl or hydrogen, and
wherein the compound is an enantiomerically pure (−) stereoisomer.

3. A compound having the chemical structure wherein $R_1$ is a lower alkyl;
$R_2$ is a lower alkyl;
$R_3$ is a halogen or lower alkyl having 1 to 3 carbons, and
wherein the compound is an enantiomerically pure (−) stereoisomer.

4. The compound of claim 3, wherein $R_3$ is a methyl and the compound comprises:

5. The compound of claim 3, wherein
$R_1$ is a methyl or propyl;
$R_2$ is a methyl or propyl; and
$R_3$ is a methyl.

6. The compound of claim 3, wherein said compound has the chemical structure

7. A method of vasoconstricting blood vessels by selectively antagonizing the CB1-like receptor, comprising administering to a subject a therapeutically effective amount of a compound sufficient to induce vasoconstriction, the compound comprising:

wherein dashed lines independently represent either a single or a double bond;
$R_1$ is a lower alkyl;
$R_2$ is a lower alkyl;
$R_3$ is a lower alkyl or halogen;
$R_4$ is a lower alkyl or hydrogen;
$R_5$ is a lower alkyl or hydrogen;
$R_6$ is a hydrogen, lower alkyl or halogen;
$R_7$ is a hydrogen, lower alkyl or halogen, and
thereby selectively antagonizing the CB1-like receptor.

8. The method of claim 7, wherein the compound comprises:

wherein dashed lines independently represent either a single or a double bond;
$R_1$ is a lower alkyl;
$R_2$ is a lower alkyl;
$R_3$ is a halogen or a lower alkyl;
$R_4$ is a lower alkyl or hydrogen; and
$R_5$ is a lower alkyl or hydrogen.

9. The method of claim 8, wherein the compound comprises:

wherein $R_1$ is a lower alkyl;
$R_2$ is a lower alkyl; and
$R_3$ is a halogen or lower alkyl.

10. The method of claim 9, wherein the compound comprises:

11. The method of claim 7, wherein the method comprises administering the compound to a subject experiencing or at risk of experiencing shock.

12. The method of claim 8, wherein the method comprises administering the compound to a subject experiencing or at risk of experiencing vasodilatory shock.

13. The method of claim 12, wherein the method comprises administering the compound to a subject experiencing or at risk of experiencing septic shock.

14. The method of claim 7, wherein the method is a method of vasoconstricting blood vessels that are dilated by the activation of a CB1-like receptor.

15. A pharmaceutical composition comprising a therapeutically effective amount of the compound of claim 1.

16. The pharmaceutical composition of claim 15, comprising an enantiomerically pure (−) stereoisomer of a compound having the chemical structure 17. A kit for vasoconstricting blood vessels in a subject comprising a container comprising the compound of claim 1.

18. The kit of claim 17, further comprising a container comprising another vasoconstrictive, inotropic, or antibiotic agent.

19. The kit of claim 18, wherein the vasoconstrictive or inotropic agent is norepinephrine, dopamine, or dobutamine.

20. The kit of claim 17, further comprising instructions for administering the compound to a subject.

21. The method of claim 7, wherein the compound is an enantiomerically pure (−) stereoisomer.

22. The method of claim 7, wherein the compound is a substantially pure antagonist of the CB1-like receptor.

23. The method of claim 7, wherein the compound does not block the CB1 receptor.

24. A selective and substantially pure antagonist of the CB1-like receptor, comprising an enantiomerically pure (−) stereoisomer having the chemical structure:

* * * * *